United States Patent [19]

Le Febre et al.

[11] Patent Number: 5,430,295
[45] Date of Patent: Jul. 4, 1995

[54] PROCESS FOR CONTROLLING BLENDING

[75] Inventors: David A. Le Febre, Camino; Linda M. Lane, Long Beach, both of Calif.

[73] Assignee: UOP and Arco, Des Plaines, Ill.

[21] Appl. No.: 167,315

[22] Filed: Dec. 16, 1993

[51] Int. Cl.[6] .................. G01N 33/28; G01N 21/35
[52] U.S. Cl. .................... 250/340; 250/339.07; 250/339.12
[58] Field of Search ............. 250/339.07, 339.08, 250/339.12, 343, 340

[56] References Cited

U.S. PATENT DOCUMENTS

| | | |
|---|---|---|
| 3,385,680 | 5/1968 | Feld et al. |
| 4,786,171 | 11/1988 | LeFebre et al. ............... 356/326 |
| 4,963,745 | 10/1990 | Maggard ......................... 250/343 |
| 5,121,986 | 6/1992 | Rutz ............................... 356/133 |
| 5,223,714 | 6/1993 | Maggard ......................... 250/343 |
| 5,225,679 | 7/1993 | Clarke et al. ................... 250/343 |

FOREIGN PATENT DOCUMENTS

| | | |
|---|---|---|
| 0285251 | 10/1988 | European Pat. Off. ......... 250/343 |
| 0305090 | 3/1989 | European Pat. Off. |
| 9115762 | 10/1991 | WIPO |

OTHER PUBLICATIONS

Kelly et al., 'Prediction of Gasoline Octane Numbers from Near-Infrared Spectral Features in the Range 660–1215 nm', Anal. Chem. 1989, 61, 313–320.

Kelly et al., 'Nondestructive Analytical Procedure for Simultaneous Estimation of the Major Classes of Hydrocarbon Constituents of Finished Gasolines', Anal. Chem. 1990, 62, 1444–1451.

Maggard "Octane", Fuel Reformation, May/Jun. 1992, pp. 71–77.

DiFoggio, R; Sadhukhan, M.; Ranc, M. L.; *Oil and Gas Journal* May 3, 1993, 87–90.

Gary, J. H.; Handwerk, G. E. *Petroleum Refinery Techniques and Economics;* Marcel Dekker: New York, 1984; Chapter 11.

Fodor, G. E.; Kohl, K. B. *Energy and Fuels,* 1993, 7, 598–601.

*Primary Examiner*—Constantine Hannaher
*Assistant Examiner*—Edward J. Glick
*Attorney, Agent, or Firm*—Thomas K. McBride; Eugene I. Snyder

[57] ABSTRACT

A process of controlling the blending of components to produce a product composition at a target value for least one characteristic has been developed. The process involves varying the proportion of the components, determining with each variation the change in the value of a characteristic, adjusting the proportion of those components to afford a new composition where the value of the characteristic is numerically closer to the target value, and repeating the steps until the target value of the characteristic is achieved. The process further includes determining blending factors to be used in existing blending equations.

34 Claims, 1 Drawing Sheet

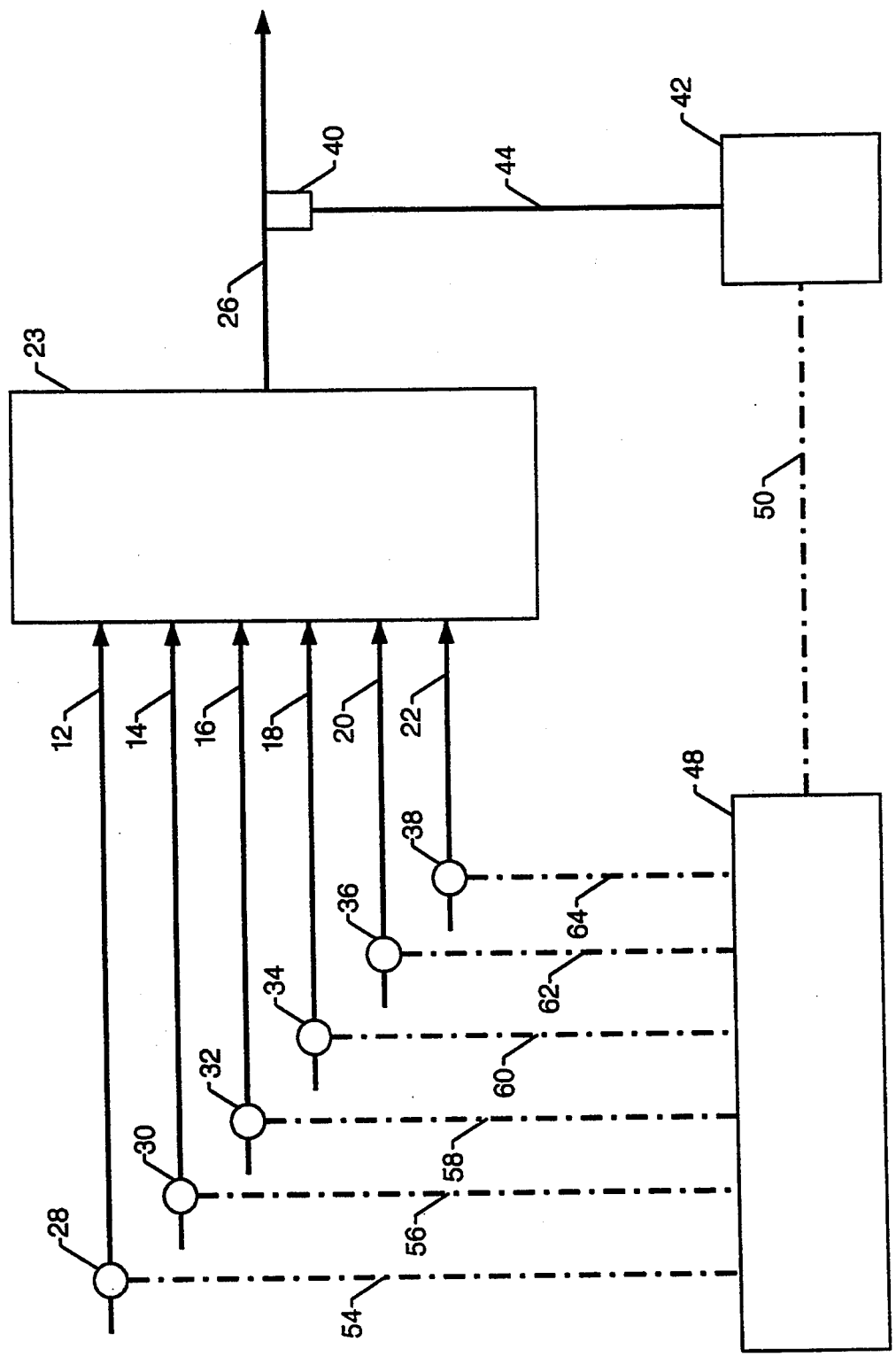

PROCESS FOR CONTROLLING BLENDING

BACKGROUND OF THE INVENTION

A common practice in petroleum refining is to blend products from several different process units, such as straight run gasoline, alkylate, hydrocrackate, reformate, oxygenates, etc., and purchased components to obtain gasoline in a grade that meets regulatory requirements such as minimum octane number, Reid vapor pressure, benzene content, and the like. Octane number, as defined by ASTM D2699 for research octane number or ASTM D2700 for motor octane number, is an indication of a gasoline's resistance to pre-ignition during the compression stroke of a piston, and Reid vapor pressure (RVP), as defined by ASTM D323, is a measure of the ease of evaporation of a gasoline and is often indicative of cold start capability.

The blending of various components to form gasoline is a complex process. Depending upon refinery configuration, anywhere from five to twelve or more different base stocks are blended to meet regulatory requirements. Furthermore, the optimization can involve numerous variables including regulated parameters, physical properties and composition of the final blend, and availability and cost of blend components.

Often in industry, the ratios of the components to be blended are determined by charts or mathematical algorithms known as "blending equations". Such blending equations are well known in the petroleum refining art and are developed or adapted by each refiner depending upon available crudes, refinery configuration, and cost and availability of blend stock components. Such equations are most frequently used in the blending of components to form a gasoline which meets regulatory requirements. Examples of blending equations and their applications are given in Cary, J. H.; Handwerk, G. F. *Petroleum Refinery Techniques and Economics;* Marcel Dekker: New York, 1984; Chapter 11.

Blending equations typically relate a quantity of gasoline, in moles/L for example, at a target value for some characteristic, such as RVP, octane, or percentage composition of oxygenates, to the quantity of each of the component streams multiplied by the measured value of that same characteristic for each component stream. Blending equations also may indicate significant nonlinearity of gasoline parameters with respect to the addition of a blend component. For example, RVP generally varies nonlinearly with the addition of butane or methanol.

Using blending equations is further complicated since the value of a characteristic in a component is not necessarily indicative of the final value of the characteristic in different blended products. For example, the value of a characteristic in the blend may be less than, equal to, or greater than the sum of the proportionate values of the characteristic in the blend components. Stated another way, a component having a high octane, may increase the octane of the final blended product by variable amounts depending on the structure of the additional components being blended. "Blending octane number" is the term typically used to express a refiner's experience as to the impact a petroleum base stock will have on the octane of the final gasoline blend. Unfortunately, the blending octane number may vary, especially when the other components of the blend are changed. Therefore, blending octane numbers are normally estimated by charts, calculated empirically, or measured after the gasoline blending is complete.

Due to the described complexities, blending component ratios are usually estimated based upon laboratory data or experience. Neither approach is entirely satisfactory, and costly overcompensation and even re-blending is common in the petroleum industry. The present invention meets the demand for an improved efficient process of controlling the value of a characteristic in a blended composition by using spectroscopic measurements which can be employed on- or in-line and in real-time. For example, even though on-line octane monitors have long been available to monitor a product's octane number, the technology of these monitors is such that each measurement requires at least 12 minutes, and during those 12 minutes the octane number of the product may have changed. Furthermore, controlling blending with these monitors is inefficient due to the 12-minute delay before the effect of each parameter change becomes known. Recently, near infrared (NIR) spectroscopy has been used to determine octane numbers of hydrocarbons thereby providing virtually instantaneous octane numbers since the analysis time is generally only about one minute. U.S. Pat. No. 4,963,745, U.S. Pat. No. 5,223,714, E.P. (0 285 251), E.P. (0 305 090), and W.O. (WO 91/15762) are typical of disclosures which teach that NIR spectroscopy may be used to determine octane number. Many methods of using NIR spectroscopy can be found in the art, and which specific method is applied in the practice of this invention is not as important as the overall contribution of the advantages of NIR spectroscopy. The same pattern of significantly improved response time of NIR spectroscopy as compared to traditional on-line analyses holds for other characteristics as well as octane. Through applying the advantages provided by on-line and in-line NIR spectroscopy in a new efficient process of controlling blending, this invention furnishes a significant cost-reducing alternative to current blending practices in the petroleum industry.

U.S. Pat. No. 4,963,745, E.P. (0 305 090), and W.O. (WO 91/15762) each focused on a specific method for using NIR spectroscopy to measure the value of a characteristic. Each also briefly disclosed that its particular method may be used to control a blending operation. However, in contrast to our invention, none of the disclosures provide the specific details of the control process necessary for one skilled in the art to implement the particular method as a control process. U.S. Pat. No. 5,223,714, disclosed using NIR to predict physical or chemical properties of the blended product from the absorbance of each preblending component. This patent disclosed that such predictions may be used to control blending, but the focus of the patent was on how to make the measurements and how to mathematically manipulate those measurements. Our invention allows any suitable spectroscopic and mathematical techniques to be used and instead focuses on the detailed steps of controlling the blending. E.P. (0 285 251) disclosed an NIR spectroscopic method to determine octane number but did not disclose using the method to control a blending operation.

SUMMARY OF THE INVENTION

The purpose of this invention is to provide a control process for a blending operation so that the final blended composition is at a target value of at least one characteristic. More specifically, the invention is directed to controlling the value of at least one characteristic during the blending of petroleum refining streams to produce a petroleum product at a target value for the characteristic. A specific embodiment of the invention is controlling the value of octane number while blending petroleum refining streams, which are variable and may in fact be varying, to produce blended gasoline of a particular octane number. A still further specific embodiment is the use of NIR spectroscopy as the analytical technique to determine the values of one or more characteristics. Still another embodiment discloses a process of more precisely determining blending octane numbers to be used in existing blending equations.

The novel features of the present invention will be better understood from the following detailed description, considered in connection with the accompanying drawing. It should be expressly understood, however, that the drawing is for the purposes of illustration and description only and is not intended as a definition of the limits of the present invention.

BRIEF DESCRIPTION OF THE DRAWING

The drawing is a schematic representation of a generic blending station such as a gasoline blending station in a petroleum refinery, modified and operated in accordance with the process of the present invention. The drawing has been simplified by the deletion of a large number of pieces of apparatus customarily employed on a process of this nature which are not specifically required to illustrate the performance of the subject invention.

DETAILED DESCRIPTION OF THE INVENTION

This invention is a process of controlling the value of at least one characteristic in a blended composition resulting from the blending of various stock components. Although many types of components may be blended to form a wide variety of products, in the typical case, the components are petroleum refinery streams which are blended to form a petroleum product. For example, the blended product may be, but is not limited to, gasoline, jet fuel, diesel fuel, lubricating oils, and others. The characteristics for which the blending is controlled may be one or more of a number of characteristics such as, but not limited to, octane number, cetane number, RVP, specific gravity, and viscosity, and percentage content of benzene, aromatics, ethers, alcohols, and others. Furthermore, additional considerations or economic weightings other than quality parameters, physical properties or compositional characteristics could also be controlled. Material costs and blending component availability, for example, could be included. Which characteristics are controlled generally depends on the desired petroleum product. For example, if the product is gasoline, the characteristics controlled may include octane number and RVP; if the product is diesel fuel, the characteristic controlled for may be cetane number; and, if the product is lubricating oil, the characteristics controlled may include viscosity.

In general terms, the apparatus necessary to perform the present invention in a typical case includes feed lines, having flow sensors and flow controllers connected to a computer, which provide the components to a mixing chamber, a product line which conducts the blended product away from the mixing chamber, and a means for analyzing the product which is also connected to the computer. Also in general terms, the invention is performed by first setting the proportion of the components to previously selected values and then determining the initial values, $V_I$, of one or more characteristics of the product. The proportions of the components are then temporarily varied, during each variation the values of the characteristics of the product are determined, and the changes in those values from the initial values are calculated. The variations in the proportions of the components may then be related to the resulting changes in the values of said characteristics by a suitable algorithm. The proportions of the components may then be adjusted according to a suitable algorithm and the values of the characteristics in the new composition, $V_N$, may then be determined. The process is repeated, varying the proportions of the components, determining the variation in the values of the characteristics, and adjusting the proportion of the components, so that the values of the characteristics in each new composition become numerically closer to the target values, $V_T$, of the characteristics. This progression can be represented as $|V_T-V_N| \leq |V_T-V_I|$. It is not necessary that the target values of the characteristics be met exactly, it is sufficient that the values of the product composition be within $\pm \delta$ of the target values. The value of $\delta$ depends on the characteristic being controlled, and is the industry accepted variability for that characteristic. For example, when the characteristic is octane number, the $\delta$ would be about 0.3 octane number and when the characteristic is RVP, the value of $\delta$ would be about 0.2 psi. The preceding steps would be repeated until $|V_T-V_N| \leq \delta$. Once this point is reached, the proceeding steps only need to be repeated periodically to verify that $|V_T-V_N|$ has not become greater than $\delta$, or when any processing change is made. It is contemplated that, the variations and adjustments would be performed automatically by way of a feedback loop responding to the results of the determinations of the values of the characteristics.

It is important to note that the amount by which the proportion of the components is varied is preferably kept sufficiently small so that each variation alters the values of the characteristics in the final blended product only slightly as compared to the previously measured blended composition. Generally, the preferred embodiment is that where the values of the characteristics are altered by about the corresponding $\delta$ or less. For example, in a preferred embodiment, the component proportion variations are preferably sufficiently small so that the value of the octane number of the final blended product is altered by only about 0.1 to about 0.3 octane numbers. Controlling the blending through such small incremental changes in the values of the characteristics is possible since the noise level of the spectroscopic measurements is surprisingly low. This invention, through capitalizing on the low noise level of the measurements and using relatively small increments, adds an increased degree of precision to the overall control. Furthermore, allowing only relatively small incremental changes in the values of the characteristics minimizes non-linear effects that may arise from the combination of the blending stock components. While it is preferred, the invention is not limited to such small variations, and larger variations which result in larger changes in the values of the characteristics, e.g., up to one octane number, are contemplated.

It is not important, however, in what order the proportions of the components are varied. In fact, although it is an option, it is not necessary that the proportion of each component be varied individually. It is within the scope of this invention to vary the proportions of the components individually, in pairs, or in groups of three or more.

Determinations of the values of the characteristics pursuant to this invention are made by first obtaining the NIR absorbance, reflectance, or transmission spectrum of the blended composition and then calculating the values of said characteristics according to a predetermined algorithm relating said characteristics to the spectrum. The actual wavelength range is not important to specify here since it is possible to use wavelengths which span the entire near infrared range of about 700 to about 2,500 nm. However, the range of about 900 to about 2,000 nm is preferred due to the superior signal to noise ratio observed when working in this range, and the range of about 1,100 to about 1,600 is most preferred. Such optical measurements are known in the art, as are several mathematical algorithms for analyzing the spectral data, including but not limited to, partial least squares with latent variables, multivariant regression, principal component regression and Gauss Jordan type row reduction. See generally, DiFoggio, R; Sadhukhan, M.; Ranc, M. L.; *Oil & Gas J.* May 3, 1993, 87–90. It is further contemplated that, where appropriate, the exact numerical values of the characteristic need not be determined. The blending control, although less efficient, may be accomplished with only the determination of whether a variation in the proportion of the components causes an increase or a decrease in the value of the characteristic.

Applying NIR spectroscopy contributes to the superior efficiency of the invention since the technique requires no sample preparation, and is accurate, rapid and non-destructive. Furthermore, NIR spectroscopy can be performed on-line, where the sample is automatically routed to the spectrophotometer, or in-line, where a probe or waveguide is placed directly in the stream. One example of a suitable optical probe is further disclosed in U.S. Pat. No. 4,786,171, which is incorporated herein by reference. Other such spectrophotometric equipment is well known in the art. The time necessary to obtain the spectrum and calculate results is generally less than one minute, and the same spectrum may be used to calculate the values of various characteristics. These factors result in data being available in real-time, which when used in the present invention translates into the ability to precisely and efficiently control the value of a characteristic.

While NIR spectroscopy is preferred, other spectroscopic techniques could be used in lieu of NIR spectroscopy. Mid-range infrared spectroscopy or Fourier-transform infrared spectroscopy may be used where the characteristic may be measured in the range of about 2,500 to about 25,000 nm. Once again, the actual wavelength range is not critical to the success of the invention since it is possible to use wavelengths that span the entire mid-range infrared and Fourier-transform infrared region. However, the most useful and therefore preferred wavelength ranges are about 2,500 to about 4,000 nm, and about 2,800 to about 3,200 nm. Examples of measurements in the mid-range infrared region may be found in Fodor, G. E.; Kohl, K. B. *Energy and Fuels,* 1993, 7, 598–601. Where appropriate, one spectroscopic technique may be substituted for another without affecting the other steps in the practice of this invention.

Without intending any limitation on the scope of the present invention, and as merely illustrative, this invention is explained below in specific terms as applied to the preferred embodiment of controlling the octane number of a blended gasoline to obtain a specific grade gasoline having a desired octane number. The necessary apparatus is first described, and then the process of the invention as applied to the preferred embodiment is discussed. For ease of understanding, the process of the invention is described below as the sequential variation of individual components and as just mentioned, control of the value of only one characteristic.

Turning now to the apparatus as illustrated in the drawing, several input lines 12, 14, 16, 18, 20, and 22 supply the stock components to the blending chamber 23 in which the stock components are mixed to form the blended gasoline. It should be understood that a greater or lesser number of input lines may be employed depending upon the blending process involved, stock components available, and the preferences of the particular refiner. The blended gasoline is conducted through an output conduit 26 to some storage facility such as a holding tank (not shown) or transferred downstream to a pipeline (not shown). Each of the input lines 12–22 is provided with an associated flow rate sensor and flow control valve, respectively indicated as a unit at 28, 30, 32, 34, 36, and 38. The output conduit 26 is provided with an optical sampling cell 40 that is coupled to a spectrophotometer 42 by a fiber optic cable or planer waveguide 44.

The spectrophotometer 42 is coupled by a data bus 50 to a general control system computer 48. Each of the flow rate sensors and flow control valves 28–38 are similarly respectively coupled to the computer 48 via data buses 54–64. The control system computer 48 monitors both the flow rates of the blending stock components through the input lines 12–22 and the data provided by the spectrophotometer 42 in order to vary the flow rates in the input lines 12–22 by appropriate commands to the associated flow control valve.

Using the described apparatus, the invention as applied to the preferred embodiment of controlling the octane number of a blended gasoline to obtain a specific grade gasoline having a desired octane number is performed as follows. The flow rates of each of the feed lines 12–22, and therefore the proportion of each component, may be first set to selected values based on the refiner's experience, laboratory data, or blending equations. The value of the initial octane number may then be determined by obtaining the NIR spectral profile of the blended gasoline flowing through the output conduit 26 over the range of 900 to 2,000 nm and analyzing the spectral profile according to, e.g., a partial least squares with latent variables type mathematical technique. The flow rate through feed line 12 might then be changed and the value of the octane number of the now altered gasoline flowing out of the mixing chamber 23 and through the output conduit 26 may be again determined using the spectrophotometer 42 to obtain and analyze a new NIR spectral profile. The flow rate through feed line 12 may then be returned to its initial setting, and the flow rate through another feed line, such as feed line 14, might be varied. The value of the octane number of the again altered blended gasoline may be again determined by obtaining and analyzing another spectral profile with the spectrophotometer 42, after which the flow rate through 14 may also be returned to its initial setting. This process may be repeated for each of the remaining feed lines 16–22 with the value of the octane number of the blended gasoline being determined after the flow rate through each feed line had been altered, and before the flow rate had been returned to its initial setting. Once each feed line has been individually and sequentially altered and the resulting effect on the value of the octane number of the blended gasoline recorded, the flow rate of one or more of the feed lines may be reset according to an algorithm to afford a product whose octane number is closer to the target value than was the octane number of the initial product. The new value of the octane number of the gasoline formed by this altered blending of the components might then be determined and the foregoing procedure repeated until the value of the octane number of the product composition is within ±0.3 octane numbers of the desired or target octane number.

It must be emphasized that the above description is merely illustrative of a preferred embodiment, and is not intended as an undue limitation on the generally broad scope of the invention. Moreover, while the description is narrow in scope, one skilled in the art will understand how to extrapolate to the broader scope of the invention. For example, the procedure for the simultaneous variation of groups of feed lines or for the simultaneous control of more than one characteristic can be readily extrapolated from the foregoing description.

In an alternative embodiment of the present invention, blending octane numbers can be directly determined and used in existing blending equations thereby improving the accuracy and usefulness of the blending equations. As previously mentioned, the blending octane number of a stock component which is applied in the blending equation, may differ in impact on the octane number of the finished blend depending on the presence or absence of other blending components. Therefore, being able to accurately determine blending octane numbers that apply specifically to the matrix of components being used allows for more accurate results from blending equations. The blending octane number of a blending stock component can be derived from:

$$[O_x][\Delta L_x] + [O_k][L_T] = [O_T][L_T + \Delta L_x] \quad [1]$$

or $$O_x = O_T + \Delta O_x[L_T/\Delta L_x] \quad [2]$$

where:
$O_x$ = the blending octane number of feed line x
$O_k$ = the octane number of the blended gasoline before any incremental change in the flow rate of feed line x
$O_T$ = the octane number of the blended gasoline after an incremental change in the flow rate of feed line x
$L_T$ = the total volume of blended gasoline
$\Delta L_x$ = the incremental volume change of feed line x
$\Delta O_x$ = the incremental change in the octane number of the blended gasoline Thus, in this embodiment of the present invention, pre-existing blending equations may be more effectively applied by using octane numbers for the blending stock components that are obtained through the application of equations [1] or [2], above. To perform this embodiment, first the flow rates for each of the feed lines x would be set to selected values, then the values of $O_k$ and $L_T$ would be measured, and finally, the flow rates for each of the feed lines would be sequentially varied with measurements of $\Delta L_x$ and $O_T$ taken and $\Delta O_x$ calculated after each change in a feed line flow rate. The blending octane numbers $O_x$ of each blending stock component could then be derived from equations [1] or [2], above. These derived blending octane numbers are specific to the matrix at hand, and using these derived blending octane numbers in existing blending equations provides more accurate results than the current practice of using blending octane numbers based on the refiner's general experience.

What is claimed is:

1. A process for continuously controlling the value of at least one characteristic of a petroleum product composition resulting from the blending of N components, where the initial value of the characteristic in the product composition is $V_I$, where the final value of the characteristic in the product composition is to be within ±δ of a target value $V_T$ and where the value of said characteristic is determined by obtaining the near infrared spectrum of the product composition over the range of about 700 to about 2,500 nm and calculating the value of said characteristic in the product composition according to a predetermined first algorithm relating said characteristic to the spectrum, comprising:
   a. varying the proportions of the components to afford a series of intermediate product compositions;
   b. determining the value of said characteristic in each of said intermediate product compositions and calculating therefrom the change in said value associated with the variation in each component proportion;
   c. adjusting the proportions of the components according to a second algorithm, said algorithm relating the variation of each component proportion to the resulting change in the value of said characteristic in said intermediate product composition, to afford a new product composition whose new value of said characteristic is $V_N$ and where $|V_T - V_N| \leq |V_T - V_I|$; and
   d. repeating steps a)–c) until $|V_T - V_N| \leq \delta$.

2. The process of claim 1 where the proportions of the components are varied by amounts affording changes in the value of said characteristic of δ or less.

3. The process of claim 1 where the characteristic is selected from the group consisting of octane number, cetane number, Reid vapor pressure, specific gravity, viscosity, aromatic content, benzene content, ether content, and alcohol content.

4. The process of claim 1 where the near infrared spectrum is obtained over the range of about 900 to about 2,000 nm.

5. The process of claim 1 where the near infrared spectrum is obtained over the range of about 1,100 to about 1,600 nm.

6. The process of claim 1 where the proportion of each component is varied singularly.

7. The process of claim 1 where the proportions of the components are varied in groups of two or more.

8. The process of claim 1 where two or more characteristics are controlled simultaneously.

9. The process of claim 1 where the near infrared spectrum is obtained on-line.

10. The process of claim 1 where the near infrared spectrum is obtained in-line.

11. The process of claim 1 where the product composition is gasoline, and where the characteristic is selected from the group consisting of octane number, Reid vapor pressure, specific gravity, viscosity, aromatic content, benzene content, ether content, and alcohol content.

12. A process for continuously controlling the value of at least one characteristic of a product composition resulting from the blending of N components, where the initial value of the characteristic in the product composition is $V_I$, where the final value of the characteristic in the product composition is to be within $\pm\delta$ of a target value $V_T$ and where the value of said characteristic is determined by obtaining a spectrum of the product composition where said spectrum is generated by a spectroscopic technique selected from the group consisting of near infrared spectroscopy over the range of about 700 to about 2,500 nm, mid-range infrared spectroscopy over the range of about 2,500 to about 25,000 nm, and Fourier-transform infrared spectroscopy over the range of about 2,500 to about 25,000 nm, and calculating the value of said characteristic in the product composition according to a predetermined first algorithm relating said characteristic to the spectrum, comprising:
 a. varying the proportions of the components to afford a series of intermediate product compositions;
 b. determining the value of said characteristic in each of said intermediate product compositions and calculating therefrom the change in said value associated with the variation in each component proportion;
 c. adjusting the proportions of the components according to a second algorithm, said algorithm relating the variation of each component proportion to the resulting change in the value of said characteristic in said intermediate product composition, to afford a new product composition whose new value of said characteristic is $V_N$ and where $|V_T-V_N| \leq |V_T-V_I|$; and
 d. repeating steps a)–c) until $|V_T-V_N| \leq \delta$.

13. The process of claim 12 where the proportions of the components are varied by amounts affording changes in the value of said characteristic of $\delta$ or less.

14. The process of claim 12 where the characteristic is selected from the group consisting of octane number, cetane number, Reid vapor pressure, specific gravity, viscosity, aromatic content, benzene content, ether content, and alcohol content.

15. The process of claim 12 where said near infrared spectroscopy range is about 900 to about 2,000 nm, said mid-range infrared spectroscopy range is about 2,500 to about 4,000 nm, and said Fourier-transform infrared spectroscopy range is about 2,500 to about 4,000 nm.

16. The process of claim 12 where said near infrared spectroscopy range is about 1,100 to about 1,600 nm, said mid-range infrared spectroscopy range is about 2,800 to about 3,200 nm, and said Fourier-transform infrared spectroscopy range is about 2,800 to about 3,200 nm.

17. The process of claim 12 where the proportion of each component is varied singularly.

18. The process of claim 12 where the proportions of the components are varied in groups of two or more.

19. The process of claim 12 where two or more characteristics are controlled simultaneously.

20. The process of claim 12 where said spectrum is obtained on-line.

21. The process of claim 12 where said spectrum is obtained in-line.

22. The process of claim 12 where the product composition is gasoline, and where the characteristic is selected from the group consisting of octane number, Reid vapor pressure, specific gravity, viscosity, aromatic content, benzene content, ether content, and alcohol content.

23. The process of determining the blending octane numbers of N components which are blended to form a blended gasoline of volume $L_T$, where the initial value of the octane number of the blended gasoline, $O_k$, is determined by obtaining the near infrared spectrum of the blended gasoline over the range of about 700 to about 2,500 nm and calculating the value of the octane number in the blended gasoline according to a predetermined algorithm relating said octane number to the spectrum, comprising:
 a. varying the proportion of said components by an amount, $\Delta L_x$, to afford a series of new blended gasolines;
 b. determining the value of the octane number in each of said new blended gasolines, $O_T$, and calculating therefrom the change, $\Delta O_x$, in said octane number associated with the variation in proportion of each component by the equation $\Delta O_x = O_k - O_T$; and
 c. determining the blending octane number, $O_x$, of each component according to the formula: $O_x = O_T + \Delta O_x [L_T/\Delta L_x]$.

24. The process of claim 23 where the proportion of a component is varied by an amount such that $\Delta O_x \leq 0.3$.

25. The process of claim 23 where the near infrared spectrum is obtained over the range of about 900 to about 2,000 nm.

26. The process of claim 23 where the near infrared spectrum is obtained over the range of about 1,100 to about 1,600 nm.

27. The process of claim 23 where the near infrared spectrum is obtained on-line.

28. The process of claim 23 where the near infrared spectrum is obtained in-line.

29. The process of determining the blending octane numbers of N components which are blended to form a blended gasoline of volume $L_T$, where the initial value of the octane number of the blended gasoline, $O_k$, is determined from a spectrum of the blended gasoline generated by a spectroscopic technique selected from the group consisting of near infrared spectroscopy over the range of about 700 to about 2,500 nm, mid-range infrared spectroscopy over the range of about 2,500 to about 25,000 nm, and Fourier-transform infrared spectroscopy over the range of about 2,500 to about 25,000 nm, and calculating the value of the octane number of the blended gasoline according to a predetermined algorithm relating said octane number to the spectrum, comprising:
 a. varying the proportion of said components by an amount, $\Delta L_x$, to afford a series of new blended gasolines;
 b. determining the value of the octane number in each of said new blended gasolines, $O_T$, and calculating therefrom the change, $\Delta O_x$, in said octane number associated with the variation in proportion of each component by the equation $\Delta O_x = O_k - O_T$; and
 c. determining the blending octane number, $O_x$, of each component according to the formula $O_x = O_T + \Delta O_x [L_T/\Delta L_x]$.

30. The process of claim 29 where the proportion of a component is varied by an amount such that $\Delta O_x \leq 0.3$ 31. The process of claim 29 where said near infrared spectroscopy range is about 900 to about 2,000 nm, said mid-range infrared spectroscopy range is about 2,500 to about 4,000 nm, and said Fourier-transform infrared spectroscopy range is about 2,500 to about 4,000 nm.

32. The process of claim 29 where said near infrared spectroscopy range is about 1,100 to about 1,600 nm, said mid-range infrared spectroscopy range is about 2,800 to about 3,200 nm, and said Fourier-transform infrared spectroscopy range is about 2,800 to about 3,200 nm.

33. The process of claim 29 where the spectrum is obtained on-line.

34. The process of claim 29 where the spectrum is obtained in-line.

* * * * *